(12) United States Patent
Towart et al.

(10) Patent No.: US 6,391,895 B1
(45) Date of Patent: May 21, 2002

(54) NITRIC OXIDE RELEASING CHELATING AGENTS AND THEIR THERAPEUTIC USE

(75) Inventors: Robertson Towart, Stoke Poges (GB); Jan Olof Gustav Karlsson, Nesoddtangen (NO); Lars Goran Wistrand; Hakan Malmgren, both of Lund (SE)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/599,862

(22) Filed: Jun. 23, 2000

Related U.S. Application Data

(63) Continuation of application No. PCT/GB98/03804, filed on Dec. 18, 1998.
(60) Provisional application No. 60/076,793, filed on Mar. 4, 1998.

(30) Foreign Application Priority Data

Dec. 23, 1997 (GB) ................................. 9727226
Mar. 13, 1998 (GB) ................................. 9805450

(51) Int. Cl.⁷ ...................... A61K 31/444; C07D 401/12
(52) U.S. Cl. ...................... 514/335; 546/261; 546/256; 546/255; 546/24; 514/333; 514/332; 514/184
(58) Field of Search .................. 514/335, 333, 514/332, 184; 546/261, 256, 255, 24

(56) References Cited

U.S. PATENT DOCUMENTS 5,250,550 A  10/1993  Keefer et al.

FOREIGN PATENT DOCUMENTS

| WO | 0 292 761 A | 11/1988 |
| WO | WO 93 20806 A | 10/1993 |
| WO | WO 95 12394 A | 5/1995 |
| WO | WO 96 31217 A | 10/1996 |
| WO | WO 96 39409 A | 12/1996 |
| WO | WO 97 49390 A | 12/1997 |
| WO | 97/49409 | * 12/1997 | ................. 514/335 |

OTHER PUBLICATIONS

Mooradian D.L. et al., "Nitric Oxide (No) Donor Molecules: Effect of No Release Rate on Vascular Smooth Muscle Cell Proliferation in Vitro", Journal of Cardiovascular Pharmacology, Jan. 1, 1995, XP000563583.

Lefer D.J.: "Myocardial Protective Actions of Nitric Oxide Doors After Myocardial Ischemia and Reperfusion", New Horizons, Feb. 1, 1995, XP000575669.

* cited by examiner

Primary Examiner—Charanjit S. Aulakh
(74) Attorney, Agent, or Firm—Royal N. Ronning, Jr.

(57) ABSTRACT

Chelating agents, in particular dipyridoxyl and aminopolycarboxylic acid based chelating agents, and their metal chelates, when linked directly or indirectly to at least one nitric oxide releasing moiety, or when use in combination with nitric oxide or a nitric oxide releasing moiety have been found to be effective in treating a variety of disorders. In particular, such compounds may be used in treating conditions associated with the presence of free radicals in the body, e.g. reperfusion injuries, and in reducing the cardiotoxicity of anti-tumor agents, e.g. anthracyclines and/or paclitaxel.

37 Claims, No Drawings

NITRIC OXIDE RELEASING CHELATING AGENTS AND THEIR THERAPEUTIC USE

This application is a continuation of pending international application number PCT/GB98/03804, filed Dec. 18, 1998, now WO 99/33823 (of which the entire disclosure of the pending, prior application is hereby incorporated by reference), which itself is a continuation-in-part of U.S. provisional application No. 60/076,793, filed Mar. 4, 1998.

The present invention relates to nitric oxide releasing compounds and their use in treating a variety of disorders, in particular conditions resulting from the presence of free radicals in the body. In particular, the invention relates to the use of such compounds in the treatment of ischaemia-related diseases, inflammatory conditions, and retroviral diseases, in anti-tumor therapy, and in cytotoxic antimicrobial treatment (e.g. to combat bacteria, parasites, etc.).

Short-lived but highly reactive free radicals have long been believed to be involved in various sorts of tissue damage, especially in ischaemia-related diseases such as stroke, cerebral injury and thrombotic diseases, and during reperfusion of ischaemic tissue such as may occur during transplantation or microsurgery. Tissue-damaging free radicals may also be produced in certain chronic diseases, for example in diabetes, and are also produced as a result of several anti-cancer treatments, such as radiation therapy or treatment with cytotoxic drugs, e.g. anthracyclines or paclitaxel (taxol).

Ischaemia-related diseases, in particular coronary artery diseases, account for the majority of deaths in Western countries. Typically, coronary narrowing is due to the formation of thromboses at the site of atherosclerotic plaques. Acute coronary thrombosis is often treated by agressive thrombolytic treatment with streptokinase or r-tPA with the object of reperfusing the obstructed artery. However, reocclusion occurs in approx. 10% of cases. Severe coronary artery disease can be ameliorated by elective by-pass surgery, with attendant perioperative risks, or in some patients by the mechanical dilation of the blood vessels by angioplasty. However, the latter treatment carries a significant risk (approx. 30–40%) of restenosis within 6 months.

The reintroduction of oxygenated blood into ischaemic cardiac tissue can, in many cases, result in various forms of cardiac dysfunction, including arrhythmias, myocardial "stunning", arterial spasm and endothelial damage (Kirschner et al. J. Amer. College of Surgeons 179: 103–117, 1994). Several studies now suggest that much of this reoxygenation damage is a result of the production of superoxide which may in turn lead to intracellular reduction of ferritin-bound Fe(III) to Fe(II) and lipid peroxidation (see Ryan & Aust, Crit. Rev. Toxicol. 22: 119, 1992). Furthermore, the production of certain free radicals, e.g. superoxide, can result in reaction with and hence reduced levels of nitric oxide. This is undesirable since nitric oxide is believed to be essential for correct endothelial function (e.g. antithrombotic activity) and for avoiding vasospasm. Nitric oxide is also believed to have cardioprotective effects (see Vegh et al. Brit. J. Pharmacol. 107: 910–911, 1992 and Lefer et al. Circulation 88: 2337–2350, 1993).

A number of anti-tumor agents are associated with adverse side-effects which severely limit their widespread use. Paclitaxel is one such agent which has shown anti-neoplastic action against a variety of malignant tissues, including those of the breast, colon, lung and ovary, as well as in malignant melonoma. However, at the high dosages required to have an anti-neoplastic effect, paclitaxel has a number of adverse side-effects which can include cardio-vascular irregularities as well as hematological and gastrointestinal toxicity.

Anthracycline antibiotics, such as doxorubicin (adriamycin), are amongst the most important of the anti-tumor agents. However, their clinical value is also limited by their cardiotoxicity, which manifests itself as congestive heart failure in 15–40% of patients undergoing therapy. The most likely mechanism for their toxicity is believed to be the production of oxygen-derived free radicals in the heart which cause membrane damage and mitochondrial damage in metabolically active tissues such as heart muscle and intestinal mucosa. Whilst there is evidence to suggest that cardiac damage during anthracycline therapy can be reduced by simultaneous administration of the iron chelator, dexrazoxane, this has been found to be toxic and as a result can only be used in relatively low dosages.

It will be appreciated that there exists a continuing need for alternative compounds capable of treating or preventing conditions generally arising from the presence of free radicals in the body, in particular compounds which are able to prevent reperfusion injuries and act as chemoprotectants during anti-cancer therapy.

In particular, there exists a need for an effective chemoprotectant which in reducing the toxic effects of anti-tumor agents, will permit higher, more effective doses of such agents to be administered.

We have now found that chelating agents linked to at least one nitric oxide releasing moiety, and their metal chelates, are particularly effective in relieving symptoms associated with reperfusion of ischaemic tissue, and in reducing the toxicity of anti-tumor agents, e.g. anthracyclines and paclitaxel.

It has also been found that certain chelating agents, e.g. dipyridoxyl and aminopolycarboxylic acid based chelating agents, and their metal chelates, either when linked directly or indirectly to at least one nitric oxide releasing moiety, or when used in combination with nitric oxide or a nitric oxide releasing moiety, are effective in treating a variety of disorders, especially conditions associated with the presence of free radicals in the body.

Thus, viewed from one aspect the invention provides the use of a chelating agent, or a metal chelate or salt thereof, capable of releasing nitric oxide in vivo in the manufacture of a therapeutic agent for use in relieving symptoms associated with reperfusion of ischaemic tissue.

In another aspect the invention provides a method of treatment of the human or non-human animal body to relieve the symptoms associated with reperfusion of ischaemic tissue, said method comprising administering to said body a chelating agent, or a metal chelate or salt thereof, capable of releasing nitric oxide in vivo.

Viewed from a further aspect the invention provides the use of a chelating agent, or a metal chelate or salt thereof, capable of releasing nitric oxide in vivo in the manufacture of a therapeutic agent for use in reducing the cardiotoxicity of an anti-tumor agent, e.g. an anthracycline drug and/or paclitaxel.

In another aspect the invention provides a method of reducing the cardiotoxicity of an anti-tumor agent administered to the human or non-human animal body, e.g. a method of reducing the cardiotoxicity of an anthracycline drug and/or paclitaxel, said method comprising administering to said body an anti-tumor agent and simultaneously, separately or sequentially a chelating agent, or a metal chelate or salt thereof, capable of releasing nitric oxide in vivo.

Viewed from another aspect the invention provides the use of a chelating agent, or a metal chelate or salt thereof, capable of releasing nitric oxide in vivo in the manufacture of a therapeutic agent for use in combating microbial infection, e.g. by virtue of a cytotoxic antimicrobial effect.

Viewed from a still further aspect the invention provides a method of treatment of the human or non-human animal body to combat microbial infection, said method comprising administering to said body a chelating agent, or a metal chelate or salt thereof, capable of releasing nitric oxide in vivo.

Examples of microbial infection suitable for prophylactic, palliative or curative treatment according to the invention include bacterial and parasitic infections, in particular protozoal infections, for example malaria, trypanosomiasis and leichmaniasis, e.g. Chagas' disease.

Viewed from another aspect the invention provides the use of a chelating agent, or a metal chelate or salt thereof, capable of releasing nitric oxide in vivo in the manufacture of a therapeutic agent for use in combating inflammatory conditions and retroviral disease.

Viewed from a still further aspect the invention provides a method of treatment of the human or non-human animal body to combat inflammatory conditions and retroviral disease, said method comprising administering to said body a chelating agent, or a metal chelate or salt thereof, capable of releasing nitric oxide in vivo.

The use of NO generating compounds as inhibitors of HIV is discussed in WO96/31217.

Preferred chelating agents for use in the invention include dipyridoxyl and aminopolycarboxylic acid based chelating agents having linked thereto at least one nitric oxide releasing moiety, and metal chelates and salts thereof. Such compounds form a further aspect of the present invention.

In an alternative embodiment of the invention, dipyridoxyl and aminopolycarboxylic acid based chelating agents which have not been linked to a nitric oxide releasing moiety may be administered in combination or concurrently with nitric oxide or a nitric oxide releasing moiety, e.g. in the treatment of conditions associated with the presence of free radicals in the body.

In a further aspect the invention thus provides a pharmaceutical composition comprising a dipyridoxyl or aminopolycarboxylic acid based chelating agent, or a metal chelate or salt thereof, together with nitric oxide or a nitric oxide releasing moiety, and at least one pharmaceutically acceptable carrier or excipient.

In a yet further aspect the invention provides a pack containing a dipyridoxyl or aminopolycarboxylic acid based chelating agent, or a metal chelate or salt thereof, and separately nitric oxide or a nitric oxide releasing moiety for simultaneous, separate or sequential use in treating conditions associated with the presence of free radicals in the body or any of the other conditions discussed above (ie. microbial infection, retroviral infection, inflammation, etc.).

In a yet still further aspect the invention provides the use of a dipyridoxyl or aminopolycarboxylic acid based chelating agent, or a metal chelate or salt thereof, together with a nitric oxide releasing moiety in the manufacture of a therapeutic agent for use in treating conditions associated with the presence of free radicals in the body or any of the other conditions discussed above (ie. microbial infection, retroviral infection, inflammation, etc.).

Examples of suitable dipyridoxyl and aminopolycarboxylic acid based chelating agents for use in the invention, and to which one or more nitric oxide releasing moieties may be linked, include those described in EP-A-290047, EP-A-299795, EP-A-71564, DE-A-3401052, EP-A-203962 and EP-A-436579, and analogues and derivatives thereof. Particular examples of dipyridoxyl chelating agents include DPDP, DPMP, PLED, DPDP-MOA and DPDP-DOA and the chelates thereof, e.g. the manganese II, manganese III and aluminium chelates. These chelating agents have the structure

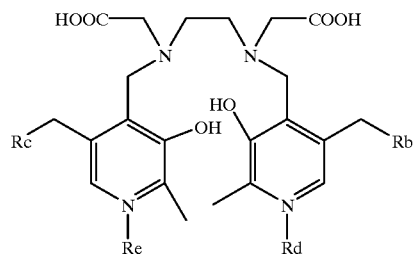

(where $R_b$, $R_c$, $R_d$ and $R_e$ have the following identities

|  | $R_b$ | $R_C$ | $R_d$ | $R_e$ |
| --- | --- | --- | --- | --- |
| DPDP | $H_2PO_4$ | $H_2PO_4$ | H | H |
| DPMP | $H_2PO_4$ | OH | H | H |
| PLED | OH | OH | H | H |
| DPDP-MOA | $H_2PO_4$ | $H_2PO_4$ | $CH_2COOH$ | H |
| DPDP-DOA | $H_2PO_4$ | $H_2PO_4$ | $CH_2COOH$ | $CH_2COOH$) |

As used herein, the term "nitric oxide releasing moiety" is intended to define any moiety capable of directly or indirectly releasing, delivering or transferring a reactive nitric oxide species, preferably a charged species, particularly nitrosonium, to another molecule in vivo, e.g. at a site of its intended activity such as on a cell membrane.

As used herein, the term "nitric oxide species" includes uncharged nitric oxide species, e.g. nitric oxide radical (NO.) and charged nitric oxide species, e.g. nitrosonium ion ($NO^+$) and nitroxyl ion ($NO^-$).

The chelating agents for use in accordance with the invention may be directly or indirectly linked to one or more nitric oxide releasing moieties, preferably up to 5, more preferably 1 to 3, e.g. 1 or 2. Thus, for example, the chelating agent may be mono- or poly-nitrosylated and/or nitrosated. It is contemplated that the nitric oxide releasing moiety itself may also be capable of the release of one or more nitric oxide species, preferably 1 to 3, e.g. 1 or 2.

Nitric oxide releasing moieties suitable for use in accordance with the invention include those described in WO-A-96/39409. Examples of suitable nitric oxide releasing moieties include 1-arginine, organic nitrates, organic nitrites, thionitrates, thionitrites, nitrosothiols, N-nitrosamines, N-oxo-N-nitrosamines, sydnonimines, diazenium diolates, 2-hydroxyimino-5-nitro-alkenamides, oxtriazolium compounds, oximes, syndomines, molsidomine, pirsidomine and other molsidomine derivatives, furoxanes, NONOates and nitrosonium salts.

Preferred nitric oxide releasing moieties include those comprising a group of the formula —$(A)_n$—B wherein A is —O—, —S—, —NR— or —$CR_2$— in which R represents hydrogen or an alkyl, cycloalkyl or aryl group, B is —NO or —$NO_2$ and n is 0 or 1. Particularly preferred nitric oxide releasing moieties are those comprising at least one —O—NO, —O—$NO_2$, —N—NO or —C—NO group.

Organic nitrates are compounds which include at least one —O—$NO_2$ group. Examples of organic nitrates suitable for use in the invention include nitroglycerine, isosorbide dinitrate, isosorbide mononitrate, sodium nitroprusside, erythritol tetranitrate and pentaerythritol tetranitrate. Isosorbide dinitrate is generally not preferred due to its toxicity.

Organic nitrites include at least one —O—NO group. Examples include isoamyl nitrite, amyl nitrite, isobutyl nitrite, and peroxynitrite:

N-nitrosamines include at least one —N—NO group. Examples include DETA NONOate and SIN-1A/γCD complex.

Nitrosothiols are compounds that include at least one —S—NO group. Examples of suitable nitrosothiols include S-nitroso-N-acetyl-penicillamine, S-nitrosocysteine and S-nitrosoglutathione.

Thionitrates suitable for use in the invention include those comprising at least one —(S)$_x$—NO group in which x is an integer of at least 2. Preferred are the dithiols in which x is 2.

C-nitroso compounds include at least one —C—NO group. Examples include streptozotocin and sydnonimines such as SIN-1.

N-oxo-N-nitrosamines suitable for use in the invention include those having at least one —NO—NO group or a —N(O$^-$M$^+$)—NO group in which M is a metal, preferably a transition metal, e.g. iron, copper, manganese or cobalt. Examples include MAHMA NONOate, NOC-5, NOC-7, NOC-12, PAPA NONOate and spermine NONOate.

Examples of diazenium diolates include DEA-NONOate, DETA-NONOate, SULFI-NONOate, SULFO-NONOate, MAHMA-NONOate, SPER-NONOate, OXI-NONOate, PAPA-NONOate, DPTA-NONOate, NOC-7, NOC-5, NOC-12, PROLI/NO and other compounds of formula A (R$_a$)$_2$N—N(O)NO (A)

(where each R$_a$ is a C$_{1-10}$ alkyl group optionally substituted by an amino, amino C$_{1-6}$ alkylamino or C$_{1-6}$ alkylamino group or the two R$_a$ groups together form an optionally carboxy substituted C$_{3-6}$ alkylene group) (see for example Sriavedra et al. J. Med. Chem 40: 1947–1954 (1997)).

Examples of oxatriazolium compounds include GEA 3162, GEA 5024 and GEA 5583.

Examples of 2-hydroxyimino-5-nitro-alkenamides include NOR-1, NOR-2 and NOR-3.

Such NO donors may be produced using techniques known from the literature and some are available commercially, e.g. from Alexis Corporation, Läufelfingen, Switzerland, e.g. DETA-NONOate, GEA3162, GEA5024, GEA5583, NOR-4, NOR-3, NOR-2, NOR-1, etc.

Further examples of NO donors include SNAP (ON—S—C(CH$_3$)$_2$CH(COOH)NHAc), Glyco-SNAP (1 and 2), SNOG (ON—S—CH$_2$CH (CONHCH$_2$COOH) NHCOCH$_2$CH$_2$CH (NH$_2$) COOH), K$_2$Ru (NO) Cl$_5$, SIN-10, Na$_2$ [Fe(CN)$_5$NO].2H$_2$O, hydroxylamine, and C$_6$H$_5$-NONOate.

NO donors have been discussed by Gasco et al. in a review article in Il Farmaco 51: 617–635 (1996) the disclosures of which are incorporated herein by reference.

Where organic nitrates are used as NO releasing moieties, a sulfhydryl-containing amino acid, such as cysteine, is preferably also used. Cysteine or other such amino acids may be conjugated to an organic nitrate to produce a sulfhydryl containing NO donor such as SPM 3672 or SPM 5185 (see EP-A-362575, EP-A-451760 and Gasco et al. Il Farmaco 51: 617–635 (1996)).

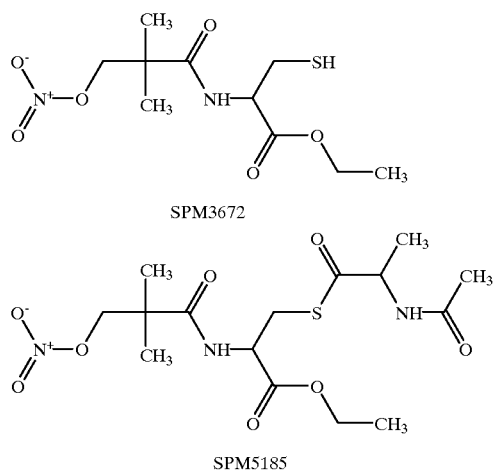

Suitable linker groups, L, used to link any given nitric oxide releasing moiety to the chelating agent include a covalent bond and an organic linker group. Preferably, L comprises an organic linker group having a molecular weight of less than 1000, preferably less than 500, e.g. less than 100.

The linker group, L, will preferably be a linear, branched or cyclic alkylene group, or any combination of such groups, or an arylene group or any combination of arylene and alkylene groups, for example providing a linking backbone 1 to 50 atoms long, preferably 2 to 10, especially 2 to 6 atoms long. The carbon backbone may be interrupted by one or more heteroatoms such as nitrogen, oxygen, sulphur, boron and phosphorus, and may carry bridging groups thereby creating homo- or heterocyclic rings within the linker moiety. If present, such rings will preferably be 3 to 12 membered, particularly preferably 5 to 8, e.g. 6-membered. Any ring present in the linker moiety, in addition to the linear backbone of the linker moiety, may optionally be substituted by one or more substituents selected from oxo, alkyl, hydroxy, alkoxy, amine, carboxyl and aryl.

Preferably, the nitric oxide releasing moiety is linked to the chelating agent via an amide, ether, ester or carbamate bond.

Preferred linker moieties include those having a linking backbone of 1 to 10 atoms, e.g. 2 to 6 atoms, in particular C$_{1-6}$ alkylene. For example, L may be CH$_2$, (CH$_2$)$_2$, (CH$_2$)$_3$ or (CH$_2$)$_4$. Especially preferably, L is (CH$_2$)$_4$.

Besides filling the role as a linker, L may be so selected as to yield a product having other desired characteristics. For example, it may be possible to increase the hydrophilicity, lipophilicity or tissue specificity of the compounds of the invention either by attachment to or incorporation within the linker moiety of a group or groups which are hydrophilic, lipophilic or tissue specific. In this way it is possible, for example, to control tissue targeting of the compounds of the invention. The linker may, for example, be substituted by a group or groups capable of attachment of the compound to a macromolecule, e.g. a biomolecule or polymer, thereby creating a bifunctional chelant.

However, the primary function of the linker moiety is to link the nitric oxide releasing moiety to the chelating agent and its precise chemical structure is of lesser importance as long as this function is fulfilled.

The exact nature of the linker group and the attached nitric oxide releasing moiety will affect both the rate of release of nitric oxide in vivo as well as the lipophilicity of the final compound. These parameters in turn will determine the onset and duration of action, as well as the absorption, distribution and pharmacokinetics of the nitric oxide releasing compound. Suitable selection of linker and nitric oxide releasing moieties can therefore be used to tailor the compounds to the desired end use.

The NO releasing group may be conjugated to the chelating agent in any convenient way. Thus for example the NO releasing group may be phosphate ester-coupled, or less preferably carboxylate ester coupled to a NO releasing group. Typical ways in which this may be achieved involve ester-coupling to a nitrogen capable of in vivo release as NO. Thus for example a phosphate group or a carboxyl group may be ester-coupled to a nitrogen in a compound such as

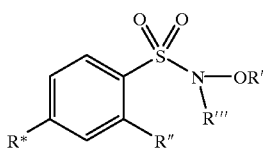

(see Lee et al. J. Med. Chem. 35: 3648–3652 (1992) and 35: 3641–3647 (1992) and Nagasawa et al. J. Med. Chem. 38: 1865–1871 (1992)).

Particularly preferred compounds for use in accordance with the invention include the dipyridoxyl based chelating agents and their metal chelates, optionally having linked thereto at least one nitric oxide releasing moiety. More particularly preferred compounds for use in the invention include derivatives of N,N'-dipyridoxyl ethylenediamine-N,N'-diacetic acid (PLED), preferably those capable of releasing nitric oxide in vivo, and metal chelates and salts thereof. Such compounds when linked to at least one nitric oxide moiety form a yet further aspect of the invention.

Accordingly, viewed from a further aspect the invention provides compounds of formula I:

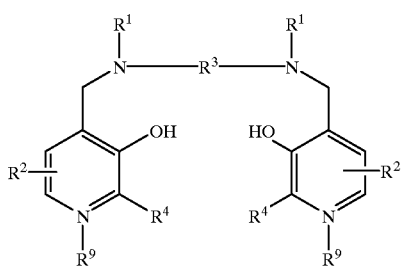

(wherein
each $R^1$ independently represents hydrogen or —$CH_2COR^5$;
$R^5$ represents hydroxy, optionally hydroxylated alkoxy, amino or alkylamido;
each $R^2$ independently represents a group —L—Z or a group —$XYR^6$, at least one group $R^2$ being a group —L—Z;
L represents a bond or an organic linker group as hereinbefore defined;
Z is a nitric oxide releasing moiety;
X represents a bond, or a $C_{1-3}$ alkylene or oxoalkylene group optionally substituted by a group $R^7$;
Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, =$NR^8$, =O, OP(O) $(OR^8)R^7$ and $OSO_3M$;
$R^7$ is hydroxy, an optionally hydroxylated, optionally alkoxylated alkyl or aminoalkyl group;
$R^8$ is a hydrogen atom or an optionally hydroxylated, optionally alkoxylated alkyl group;
$R^9$ is absent or is a hydrogen atom, or an alkyl group optionally substituted by a carboxyl or hydroxy group;
M is a hydrogen atom or one equivalent of a physiologically tolerable cation, e.g. an alkali or alkaline earth cation, an ammonium ion or an organic amine cation, such as a meglumine ion;
$R^3$ represents a $C_{1-8}$ alkylene group, preferably a $C_{1-6}$, e.g. a $C_{2-4}$ alkylene group, a 1,2-cycloalkylene group, or a 1,2-arylene group; and
each $R^4$ independently represents hydrogen or $C_{1-3}$ alkyl) and metal chelates and salts thereof.

As used herein the terms "alkyl" and "alkylene" include both straight-chained and branched, saturated and unsaturated hydrocarbons. The term "1,2-cycloalkylene" includes both cis and trans cycloalkylene groups and alkyl substituted cycloalkylene groups having from 5–8 carbon atoms. The term "1,2-arylene" includes phenyl and napthyl groups and alkyl substituted derivatives thereof having from 6 to 10 carbon atoms.

Unless otherwise specified, any alkyl, alkylene or alkenyl moiety may conveniently contain from 1 to 20, preferably 1–8, more preferably 1–6 and especially preferably 1–4 carbon atoms.

Cycloalkyl, aryl and aralkyl moieties may conveniently contain 3–18, preferably 5–12 and especially preferably 5–8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

Preferred compounds of the invention include those of formula I in which $R^5$ is hydroxy, $C_{1-8}$ alkoxy, ethylene glycol, glycerol, amino or $C_{1-8}$ alkylamido. Preferably each group $R^1$ represents —$CH_2COR^5$ in which $R^5$ is hydroxy.

In the compounds of formula I, X is preferably a bond or a group selected from $CH_2$, $(CH_2)_2$, CO, $CH_2CO$, $CH_2CH_2CO$ or $CH_2COCH_2$. Preferably, Y represents a bond.

The compounds of formula I may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Preferred compounds are those in which both $R^2$ groups represent a group —L—Z. Compounds in which the $R^2$ groups are identical and identically located, e.g. 6,6', are especially preferred.

Preferred as groups $R^6$ are mono- or poly(hydroxy or alkoxylated) alkyl groups or a group of the formula OP (O) $(OR^8) R^7$.

$R^7$ is preferably hydroxy or an unsubstituted alkyl or aminoalkyl group.

Particularly preferred identities for group $R^2$ include $CHR^7OCO(CH_2)_xPh$ and $CHR^7OCO (CH_2CO)_xPh$ (wherein x is 1 to 3), $CHR^7OCOBu^t$, $CH_2N(H)R^{6'}$, $CH_2N(R^{6'})_2$, $N(H)R^{6'}$, $N(R^{6'})_2$, $CH_2OH$, $CH_2OR^{6'}$, $COOR^{6'}$, $CON(H)R^{6'}$, $CON(R^{6'})_2$ or $OR^{6'}$ (where $R^{6'}$ is a mono- or polyhydroxylated, preferably $C_{1-4}$, especially preferably $C_{1-3}$, alkyl group), $(CH_2)_nCOOR^{7'}$ (wherein n is 1 to 6), $COOR^{7'}$ (where $R^{7'}$ is a $C_{1-4}$ alkyl, preferably $C_{1-3}$, especially preferably a methyl group), $CH_2OSO_3^-M$, $CH_2CH_2COOH$, $CH_2OP(O)(OH)(CH_2)_3NH_2$, $CH_2OP(O)(OH)CH_3$ or $CH_2OP(O)(OH)_2$ group). Yet more preferably, $R^2$ represents a group of the formula $CH_2OP(O)(OH)_2$.

Compounds of formula I in which $R^3$ is ethylene are particularly preferred.

Other chelating agents suitable for use in accordance with the invention include the macrocyclic and more preferably linear or branched aminopolycarboxylic acid chelants of EP-A-299795, EP-A-71564, DE-A-3401052, EP-A-203962, EP-A-436579 and the phosphorus oxyacid analogs, optionally having linked thereto at least one nitric oxide releasing moiety, and metal chelates and salts thereof. Such compounds when linked to at least one nitric oxide releasing moiety form a yet further aspect of the present invention.

Particularly preferred aminopolycarboxylic acid chelants include the chelating agents DTPA and EDTA, e.g. those having linked thereto at least one nitric oxide releasing moiety, and metal chelates and salts thereof, in particular amides thereof in which the nitrogens of the amide groups may be substituted by one or more $C_{1-18}$ alkyl groups, e.g. DTPA.BMA and EDTA.BMA.

Preferred metal chelates of the compounds for use in the method of the invention are those in which the metal ions are selected from the alkali and alkaline earth metals and from those metals having an atomic number from 22–31, 42, 44 and 58–70 and more particularly chelates having a $K_a$ in the range from $10^9$ to $10^{25}$, preferably $10^{10}$ to $10^{24}$, more preferably $10^{11}$ to $10^{23}$, e.g. $10^{12}$ to $10^{22}$. Particularly preferred chelates are those with metals other than iron which have a $K_a$ value smaller, preferably by a factor of at least $10^3$, than the $K_a$ value of the corresponding iron ($Fe^{3+}$) chelate. Suitable ions include $Na^+$, $Mn^{2+}$, $Ca^{2+}$, $Zn^{2+}$, $Cu^{2+}$, $Cu^+$, $Gd^{3+}$ and $Mg^{2+}$. $Mn^{2+}$ is especially preferred.

As chelates of aminopolycarboxylic acids, MnDTPA, MnEDTA, MnDTPA.BMA and MnEDTA.BMA, e.g. having linked thereto at least one nitric oxide releasing moiety, are particularly preferred for use in accordance with the invention.

More particularly preferred for use in accordance with the invention is the compound N,N'-bis-(pyridoxal-5-phosphate)-ethylenediamine-N,N'-diacetic acid or N,N'-bis(3-hydroxy-2-methyl-5-phosphonomethyl-4-pyridyl-methyl)-ethylenediamine-N,N'-diacetic acid (hereinafter referred to as DPDP) and the manganese (II) chelate, Mn(DPDP), especially such compounds in which either one or both of the phosphate groups is replaced by a nitric oxide releasing moiety.

If not all of the labile hydrogens of the chelates are substituted by the complexed metal ion, biotolerability and/or solubility of the chelate may be increased by substituting the remaining labile hydrogen atoms with physiologically biocompatible cations of inorganic and/or organic bases or amino acids. Examples of suitable inorganic cations include $Li^+$, $K^+$, $Na^+$ and especially $Ca^{2+}$. Suitable organic cations include ammonium, substituted ammonium, ethanolamine, diethanolamine, morpholine, glucamine, N,N,-dimethyl glucamine, lysine, arginine or ornithine.

The compounds herein described may be prepared by methods known in the art. Suitable methods for preparing the aminopolycarboxylic acid based chelating agents are described in EP-A-299795, EP-A-71564, DE-A-3401052, EP-A-203962 and EP-A-436579.

In preparing the dipyridoxyl compounds, the compound PLED may be used as a starting material and may be appropriately derivatised using conventional procedures to obtain the compounds of formula I. Suitable methods for preparing PLED and its derivatives are described for example in EP-A-290047.

The compounds for use in the invention linked to at least one nitric oxide releasing moiety may be prepared by conventional synthetic techniques, conveniently starting from the corresponding chelant, optionally attaching this to a linker molecule, followed by the introduction of a nitric oxide releasing group.

Viewed from a further aspect the invention provides a process for the preparation of compounds of formula I, said process comprising at least one of the following steps:

(a) reacting a compound of formula I as hereinbefore defined in which at least one group $R^2$ is a group —$CH_2OH$ with a compound of formula II:

Lv—L—Z   (II)

(where L and Z are as hereinbefore defined, and Lv is a displaceable leaving group, for example a halogen atom, such as chlorine, bromine or iodine, or a substituted sulphonyloxy group, such as methanesulphonyloxy, phenylsulphonyloxy or p-toluenesulphonyloxy);

(b) reacting a compound of formula III

(III)

with a diamine of formula (IV)

$H_2N—R^3—NH_2$   (IV)

(wherein $R^3$ and $R^4$ are as hereinbefore defined and $R^{2'}$ is an optionally protected group $R^2$ as hereinbefore defined);

(c) hydrogenating a compound of formula (V) obtained in step (b)

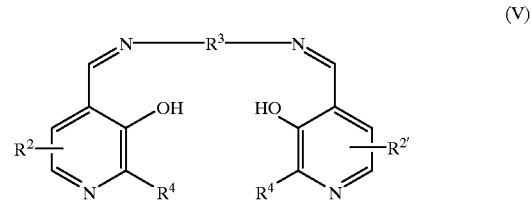

(V)

(wherein $R^3$, $R^4$ and $R^{2'}$ are as hereinbefore defined);

(d) reacting a compound of formula I (wherein one or both $R^9$ groups is absent) or a compound of formula V with a reagent serving to introduce $R^9$ groups, e.g. an acid or a compound $R^9Lv$ where Lv is a leaving group;

(e) converting a compound of formula I into a chelate complex or salt thereof.

(f) metallating or transmetallating a compound of formula I;

(g) converting a compound of formula I or a chelate thereof into a base or acid addition salt thereof or converting a salt into the free acid or base; and (h) performing at least one of steps (a) to (f) above using reagents with protected functional groups and subsequently removing the protecting groups.

In steps (a) and (b), the starting compounds are either known from the literature or can be produced by conventional synthetic techniques.

The reaction of steps (a) and (b) may conveniently be performed in a suitable solvent, such as an alcohol (e.g. methanol) at a temperature in the range of from 0 to 60° C.

To obtain compounds of formula I where the $R^2$ groups are the same, a diamine of formula IV may be reacted with two molar equivalents of a compound of formula III. For the preparation of compounds of formula I where the $R^2$ groups are different, the diamine of formula IV is first reacted with a first compound of a formula III having a desired $R^{2'}$ group, and the reaction product thereby obtained is then reacted with a second compound of formula III bearing a different $R^2$ group.

The hydrogenation of step (c) may be performed using conventional procedures, e.g. using a palladium or platinum catalyst.

The following reaction schemes useful in preparing compounds of formula I are provided by way of example:

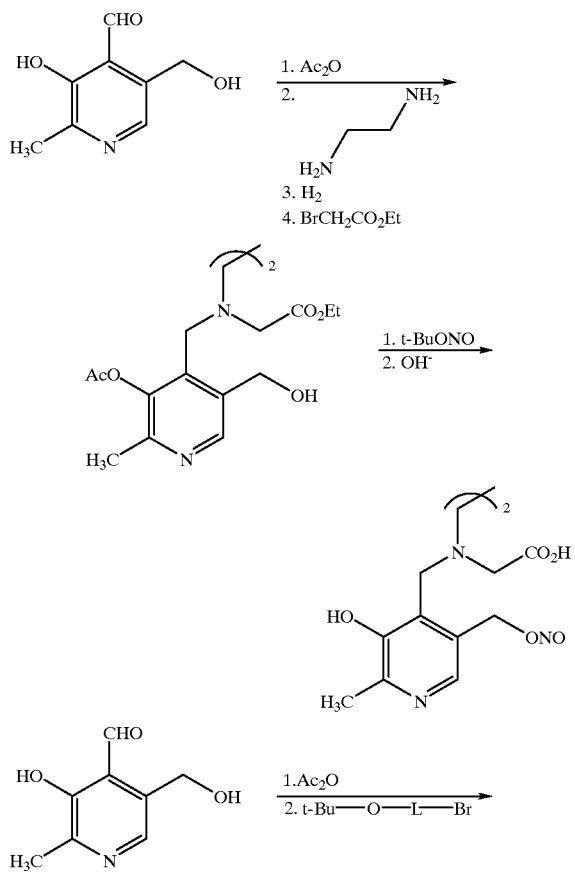

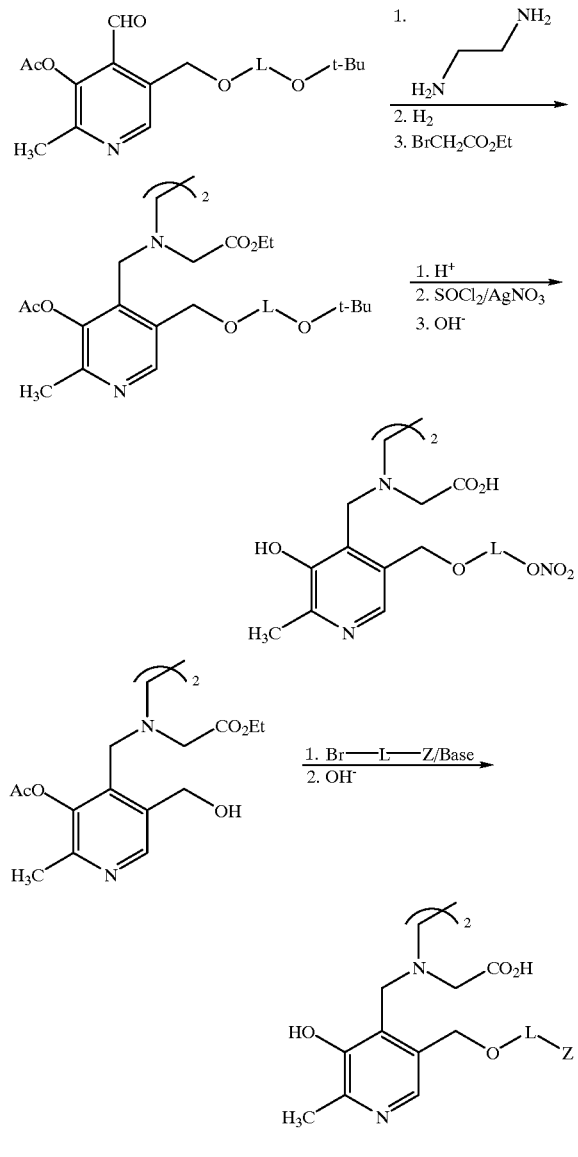

The metal chelates for use in accordance with the invention may be formed by conventional procedures known in the art. In general, such processes involve disssolving or suspending a metal oxide or metal salt (e.g. nitrate, chloride or sulfate) in water or a lower alcohol such as methanol, ethanol or isopropanol. To this solution or suspension is added an equimolar amount of the chelating agent in water or a lower alcohol and the mixture is stirred, if necessary with heating moderately or to the boiling point, until the reaction is completed. If the chelate salt formed is insoluble in the solvent used, the reaction product is isolated by filtering. If it is soluble, the reaction product is isolated by evaporating to dryness, e.g. by spray drying or lyophilising.

If acid groups such as the phosphoric acid groups are still present in the resulting chelate, it is advantageous to convert the acidic chelate salt into a neutral chelate salt by reaction with inorganic and/or organic bases or amino acids, which form physiologically acceptable cations, and to isolate them.

The carboxylic and phosphoric acid groups of the chelating agents can also be neutralised by esterification to prepare carboxylate and phosphate esters. Such esters can be prepared from the corresponding alcohols by conventional procedures known in the art. Suitable esters include, for example, esters of straight-chained or branched alcohols having from 1 to 18 carbon atoms, mono and polyhydric alkyl amino alcohols having from 1 to 18 carbon atoms, preferably having from 1 to 6 carbons, such as serinol or diethanolamine, and polyhydric alcohols having from 1 to 18 carbon atoms, such as ethylene glycol or glycerol.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The compounds and compositions herein described, in particular the compounds of formula I, are effective in treating a variety of disorders.

Viewed from a further aspect the invention thus provides a pharmaceutical composition comprising a compound of formula I, together with at least one pharmaceutical or veterinary carrier or excipient.

The compounds and compositions hereinbefore described are particularly effective in the treatment or prevention of reperfusion-induced injuries, such as arrhythmias and endothelial damage which may occur during thrombolytic treatment, after reperfusion in cardio-pulmonary bypass or following percutaneous transluminal coronary angioplasty (PTCA), and in cardiac surgery, including cardiac transplantation. A preferred use of the compounds and compositions herein described is in reducing myocardial reperfusion injury, e.g. following myocardial infarction arising from severe or acute myocardial ischemia. In particular, these are capable of providing immediate cardioprotection and subsequent reduction of restenosis and reocclusion when administered before, during or after coronary angioplasty.

The compounds and compositions as herein described are effective if administered following reperfusion of ischemic tissue. However, these are also effective to prevent reperfusion-induced injury, e.g. following myocardial ischemia, if administered after the onset of interruption in coronary blood flow but prior to the onset of reperfusion. As a result, the method of the invention is applicable not only to cases where myocardial ischemia is expected, e.g. during cardio-pulmonary bypass, PTCA and in cardiac surgery, but also in cases where myocardial ischemia is not planned, e.g. during cardiac arrest and during thrombolysis. In this regard, the compounds and compositions herein described are particularly useful as an adjunct to thrombolysis.

Viewed from a further aspect the invention thus provides a pharmaceutical composition comprising a chelating agent carrying at least one nitric oxide releasing moiety, in particular a compound of formula I, or a metal chelate or salt thereof, together with one or more thrombolytic agents, and at least one pharmaceutically acceptable carrier or excipient.

Viewed from a yet still further aspect the invention provides a pack containing a chelating agent carrying at least one nitric oxide releasing moiety, in particular a compound of formula I, or a metal chelate or salt thereof, and separately a thrombolytic agent for simultaneous, separate or sequential use during a thrombolytic procedure.

In another aspect the invention provides the use of a chelating agent carrying at least one nitric oxide releasing moiety, in particular a compound of formula I, or a metal chelate or salt thereof, together with one or more thrombolytic agents in the manufacture of a medicament for use during a thrombolytic procedure.

The invention further provides a method of treatment of a human or non-human animal body, said method comprising administering to said body an effective amount of a chelating agent carrying at least one nitric oxide releasing moiety, in particular a compound of formula I, or a metal chelate or salt thereof, and a thrombolytic agent, simultaneously, separately or sequentially during a thrombolytic procedure.

Examples of thrombolytic agents suitable for use in accordance with the invention include aspirin, plasmin, prourokinase, streptokinase, tissue plasminogen activator, urokinase, hirudin and anti-platelet drugs.

The compounds and compositions of the invention may also be used to prevent platelet deposition and thrombus formation, for example on artificial surfaces which come into contact with blood. In this regard, the compounds of the invention may be administered systemically. Alternatively, artificial surfaces which come into contact with blood, e.g. catheters, artificial heart valves, renal and other stents or vascular grafts, prostheses, etc. may be contacted or coated with a compound or composition of the invention. Damaged arterial surfaces within the vascular system are also highly susceptible to thrombus formation. In addition, the compounds and compositions of the invention may be applied directly to a damaged vascular surface, thereby preventing platelet deposition or thrombus formation on the damaged surface.

A further use of the compounds of the invention is in relation to organ transplantation, e.g. with cardiac, liver, kidney or brain transplants. In this regard, the compounds and compositions may be administered to the organ donor or recipient either prior to, during or subsequent to transplant surgery. A preferred use of the compounds is as an organ transplant solution in which organs may be stored prior to transplantation.

The compounds and compositions herein described are also effective in treating angina pectoris and other atherosclerotic-related diseases. Chronic use of such compounds is effective in the regression of atherosclerotic plaques which cause obstruction.

The compounds are also effective in sensitising hypoxic cells to radiation during anti-cancer therapy, in treating or preventing pro-inflammatory disorders, particularly in treating or preventing radiation-induced injury, e.g. in radiotherapy.

A particularly preferred use of the compounds and compositions of the invention is as cardio-protective agents and such use extends not only to use in conjunction with drugs having cardiotoxic side effects, but also to the treatment or prevention of pathological conditions in which the heart is at risk. Thus, for example, the compounds herein described may be used in the prevention or treatment of the cardiotoxic side effects of anti-tumor drugs, in particular the toxicity of the anthracyclines, such as doxorubicin. In this regard, the compounds of the invention may be administered as a combined preparation with the anti-tumor drug. Alternatively, they may be administered separately, prior to, during or subsequent to administration of the anti-tumor drug.

As used herein, the term 'anthracyclines' includes natural and semi-synthetic anthracyclines, e.g. epirubicin, idarubicin, daunorubicin and, in particular, doxorubicin and salts thereof, as well as synthetic anthracyclines, e.g. mitoxantrone, and salts thereof.

Viewed from a further aspect the invention thus provides a pharmaceutical composition comprising a chelating agent, or a metal chelate or salt thereof, capable of releasing nitric oxide in vivo, together with one or more anthracyclines, e.g. doxorubicin, and/or paclitaxel, and at least one pharmaceutically acceptable carrier or excipient.

Viewed from a yet still further aspect the invention provides a pack containing a chelating agent, or a metal chelate or salt thereof, capable of releasing nitric oxide in vivo and separately an anthracycline and/or paclitaxel for simultaneous, separate or sequential use in anti-tumor therapy.

In another aspect the invention provides the use of a chelating agent or a metal chelate or salt thereof capable of releasing nitric oxide in vivo together with one or more anthracyclines and/or paclitaxel in the manufacture of medicaments for simultaneous, separate or sequential administration in anti-tumor therapy.

In relation to the use of paclitaxel as the anti-tumor agent, it is preferable that patients are premedicated with steroids, antihistamines and/or $H_2$-antagonists to avoid hypersensitivity reactions, in particular anaphylactic reactions. Furthermore, myelotoxicity associated with paclitaxel administration, particularly with high doses of paclitaxel, can be substantially reduced by co-administration of granulocyte-colony stimulating factor (G-CSF), preferably given as a daily injection up to 24 hours after paclitaxel administration.

Other uses of the compounds herein described extend to cytotoxic and cytostatic effects on parasites, prevention of heat shock, prevention of muscle wasting and cachexia, treatment or prevention of pulmonary hypertension, treatment of septic shock, treatment of crohn's disease, inhibition of proliferation of melanoma cells, and treatment of impotence.

The therapeutic agents of the present invention may be formulated with conventional pharmaceutical or veterinary formulation aids, for example stabilizers, antioxidants, osmolality adjusting agents, buffers, pH adjusting agents, lubricating agents, wetting agents, emulsifying agents, suspending agents, preserving agents, sweetening agents etc. Administration may be by any suitable method known in the art, including for example oral, parenteral (e.g. intramuscular, subcutaneous, intraperitoneal or intravenous), rectal or topical administration. Thus the agent of the present invention may be in a conventional pharmaceutical administration form such as a tablet, capsule, powder, solution, suspension, dispersion, syrup, suppository, etc. However, solutions, suspensions and dispersions in physiologically acceptable carrier media, for example water for injections, will generally be preferred.

The compounds according to the invention may therefore be formulated for administration using physiologically acceptable carriers or excipients in a manner well-known to those skilled in the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (e.g. tromethamine hydrochloride), additions (e.g. 0.01 to 10 mole percent) of chelants (such as, for example, DTPA, DTPA-bisamide or non-complexed chelants of formula I) or calcium chelate complexes (e.g. calcium DTPA, CaNaDTPA-bisamide, calcium salts or chelates of chelants of formula I), or, optionally, additions (e.g. 1 to 50 mole percent) of calcium or sodium salts (e.g. calcium chloride, calcium ascorbate, calcium gluconate or calcium lactate combined with metal chelate complexes of chelating agents according to the invention and the like).

If the compounds are to be formulated in suspension form, e.g. in water or physiological saline for oral administration, a small amount of soluble chelate may be mixed with one or more of the inactive ingredients traditionally present in oral solutions and/or surfactants and/or aromatics for flavouring.

The preferred modes for administering the metal chelates in accordance with the invention are oral and parenteral, e.g. intravenous or intra-arterial administration. Parenterally administrable forms, e.g. intravenous solutions, should be sterile and free from physiologically unacceptable agents, and should have low osmolality to minimize irritation or other adverse effects upon administration, and thus the compositions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions may contain preservatives, antimicrobial agents, buffers and antioxidants conventionally used for parenteral solutions, excipients and other additives which are compatible with the chelates and which will not interfere with the manufacture, storage or use of the products.

The therapeutic agent in accordance with the invention, if in solution, suspension or dispersion form, will generally contain the chelant or metal chelate at a concentration in the range of from 0.0001 to 5.0 moles per litre, preferably 0.01 to 0.1 moles per litre. If convenient, the therapeutic agent may however be supplied in a more concentrated form for dilution prior to administration.

The precise dosage of the therapeutic agent and the length of the treatment will depend upon a number of factors including the age and weight of the patient, the specific condition being treated and its severity, and the route of administration. In general, the therapeutic agent in accordance with the invention may conveniently be administered in amounts of from $10^{-2}$ to 100 $\mu$mol of the compounds per kilogram of body weight, e.g. about 10 $\mu$mol per kg bodyweight. For oral administration the dosages required will be higher than for parenteral administration since uptake from the gut is unlikely to be complete.

The invention will now be illustrated further by way of the following non-limiting Examples.

EXAMPLE 1

The NO releasing N,N'-dipyridoxyethylenediamine-N,N'-diacetic acid shown below is synthesised according to the following synthetic sequence:

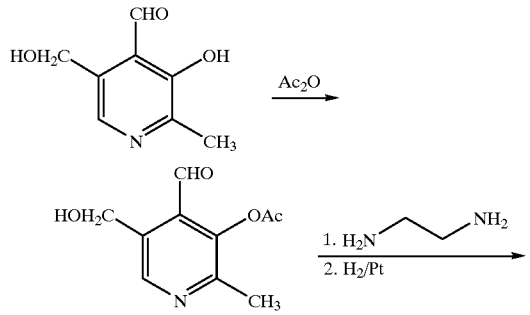

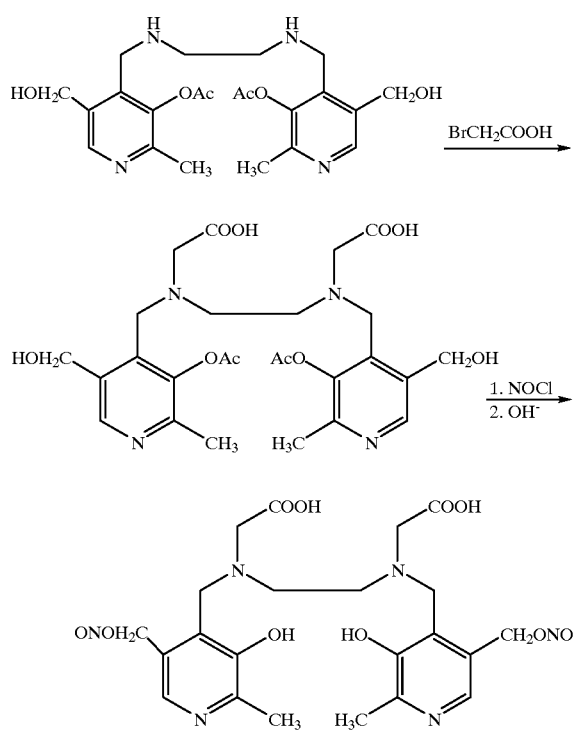

In step 1 of the reaction, pyridoxal hydrochloride is acetylated by stirring at room temperature in a solution of acetic anhydride. The solvent is evaporated and the product is purified by recrystallization. In step 2, the acetate ester is reacted with 1,2-diaminoethane in methanol analogous to a literature procedure (see U.S. Pat. No. 5,223,243). The crude imine is not isolated but reduced immediately by hydrogenation using a Pt/C catalyst (5%) in methanol to the corresponding diamine, again using a methodology described in U.S. Pat. No. 5,223,243. The crude product is precipitated from an aqueous solution by the addition of formic acid, filtered and dried. In step 3, the diamine is dissolved in water and pH is adjusted to 7. A solution of bromoacetic acid in ethanol is added dropwise while maintaining the pH, at 7 by addition of an aqueous solution of sodium carbonate. The product is extracted into diethyl ether, the organic solvent is washed with water, dried and evaporated. The crude product is purified by chromatography. In the next step, the free alcohol groups are converted into nitrite groups (for a review of synthetic methods for conversion of alcohol groups into nitrite esters see Houben-Weyl: Methoden der organischen Chemie, Band E16c, page 6). The diol is dissolved in pyridine and gaseous nitrosyl chloride is introduced at 0° C. After stirring for 10 minutes at this temperature, the solvent is removed by evaporation and the residue is hydrolyzed by treatment with a solution of sodium hydroxide in a mixture of ethanol and water. The final product is purified by chromatography or recystallization or a combination thereof.

EXAMPLE 2

An extension of the synthetic method used in Example 1 may be used for the synthesis of a nitrate ester of dipyridoxyethylenediamine-N,N'-diacetic acid as outlined in Scheme 2 (for a review of synthetic methods for conversion of alcohol groups into nitrate esters see Houben-Weyl: Methoden der Organischen Chemie, Band E16c, page 47). The diol, produced in step 3 of Example 1, is dissolved in THF. Silver nitrate is then added followed by a dropwise addition of thionyl chloride and the mixture is stirred overnight at ambient temperature. Water is added and the mixture is extracted with ethyl acetate. The organic solvent is removed by evaporation and the residue is subjected to a mild hydrolysis in an ethanol/water mixture using sodium hydroxide. The final product is purified by recrystallization or chromatography or a combination thereof.

Scheme 2

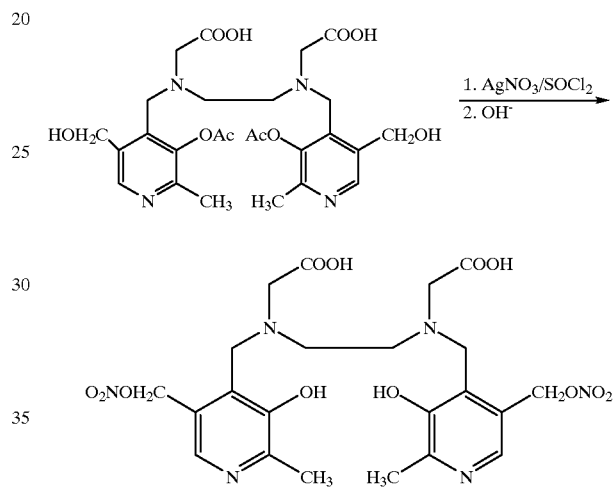

EXAMPLE 3

An alkylated PLED is prepared according to synthetic scheme outlined in Scheme 3 below. The monoacetylated pyridoxal hydrochloride produced in step 1 of Example 1 is alkylated using sodium hydride in DMSO with 1-bromo-2-t-butoxyethane. The crude product is isolated by extraction and then reacted with 1,2-diaminoethane followed by reduction of the formed imine with hydrogen using a Pt/C catalyst as described in Example 1. Alkylation of the product with 2-bromoacetic acid is also carried out following this methodology. The t-butyl groups are then removed by stirring the product in a solution of formic acid for 24 hours. The free alcohol groups are then converted into nitrite esters using a procedure analogous to that described in Example 1. Finally, the acetate groups are hydrolyzed under basic conditions and the final product is isolated by recrystallization or chromatography or a combination thereof.

Scheme 3

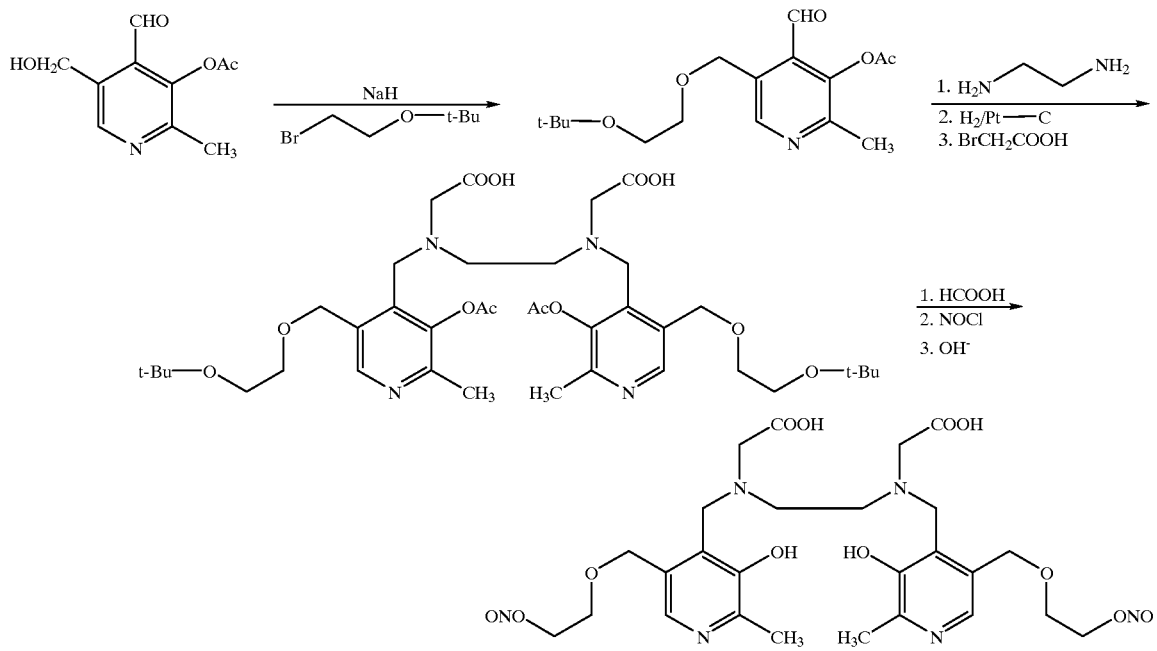

EXAMPLE 4

A furoxane containing PLED is prepared using a method analogous to that described in Example 3 as outlined in Scheme 4. The furoxane CAS1609 (described by H. Bohn et al. in Br. J. Pharmacol. 114: 1605, 1995) is tosylated by treatment with a mixture of tosyl chloride in pyridine in dichloromethane. Alkylation of monoacetylated pyridoxal hydrochloride with this tosylate is then carried out by treatment with sodium hydride in DMSO analogous to the method described in Example 3. The remaining chemical transformations are then carried out analogous to the corresponding steps as described in Example 3. The final product is purified by recrystallization or chromatography or a combination thereof.

Scheme 4

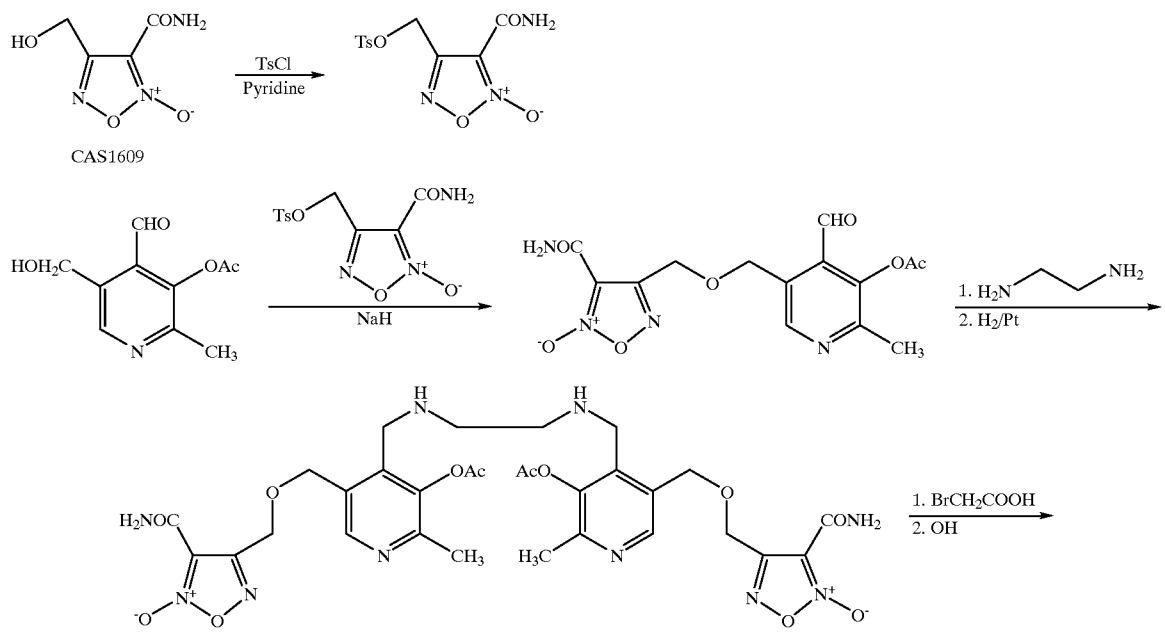

-continued

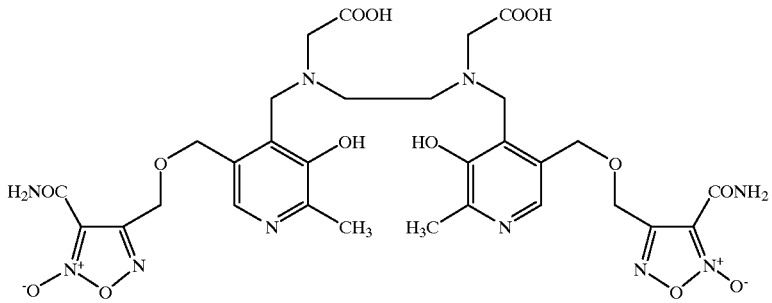

What is claimed is:

1. A method of treatment of the human or non-human animal body, to combat or prevent conditions resulting from the presence of free radicals in said body and/or to combat microbial infection and/or to combat inflammatory conditions or retroviral disease, said method comprising administering to said body a therapeutically effective amount of a dipyridoxyl chelating agent, or a metal chelate or salt thereof, capable of releasing nitric oxide in vivo.

2. Method as claimed in claim 1 for the treatment or prophylaxis of a reperfusion-induced injury.

3. Method as claimed in claim 2 wherein said injury is a result of myocardial reperfusion.

4. Method as claimed in claim 2 wherein said injury is associated with a thrombolytic procedure, a cardiopulmonary bypass, percutaneous transluminal coronary angioplasty, or is a result of cardiac or transplantation surgery.

5. Method as claimed in claim 1 for the treatment or prophylaxis of radiation-induced injury.

6. Method as claimed in claim 1 for combating malaria, trypanosomiasis or leichmaniasis.

7. Method as claimed in claim 1 wherein said chelating agent, or metal chelate or salt thereof, is linked directly or indirectly to at least one nitric oxide releasing moiety.

8. Method as claimed in claim 7 wherein said nitric oxide releasing moiety is selected from the group consisting of I-arginine, organic nitrates, organic nitrites, thionitrates, thionitrites, nitrosothiols, N-nitrosamines, N-oxo-N-nitrosamines, sydnonimines, diazenium diolates, 2-hydroxyimino-5-nitro-alkenamides, oxatriazolium compounds, oximes, syndomines, molsidomine and derivatives thereof, pirsidomine, furoxanes, NONOates and nitrosonium salts.

9. Method as claimed in claim 7 wherein said nitric oxide releasing moiety comprises a group of the formula —(A)$_n$—B wherein A is —O—, —S—, —NR— or —CR$_2$— in which R is hydrogen or an alkyl, cycloalkyl or aryl group, B is —NO or —NO$_2$ and n is 0 or 1.

10. Method as claimed in claim 7 wherein said nitric oxide releasing moiety comprises at least one —O—NO, —O—NO$_2$, —N—NO or —C—NO group.

11. Method as claimed in claim 7 wherein said nitric oxide releasing moiety is selected from the group consisting of nitroglycerine, isosorbide dinitrate, isosorbide mononitrate, sodium nitroprusside, erythritol tetranitrate, pentaerythritol tetranitrate, isoamyl nitrite, amyl nitrite, isobutyl nitrite, peroxynitrite, DETA NONOate, SIN-1A/γCD complex, S-nitroso-N-acetyl-penicillamine, S-nitrosocysteine, S-nitrosoglutathione, streptozotocin, SIN-1, MAHMA NONOate, NOC-5, NOC-7, NOC-12, PAPA NONOate, spermine NONOate, DEA-NONOate, DETA-NONOate, SULFI-NONOate, SULFO-NONOate, MAHMA-NONOate, SPER-NONOate, OXI-NONOate, PAPA-NONOate, DPTA-NONOate, NOC-7, NOC-5, NOC-12, PROLI/NO, compounds of formula A:

$$(R_a)_2N-N(O)NO \qquad (A)$$

(wherein each $R_a$ is a $C_{1-10}$ alkyl group optionally substituted by an amino, amino $C_{1-6}$ alkylamino or $C_{1-6}$ alkylamino group or the two $R_a$ groups together form an optionally carboxy substituted $C_{3-6}$ alkylene group), GEA 3162, GEA 5024, GEA 5583, NOR-1, NOR-2, NOR-3, SNAP (ON—S—C(CH$_3$)$_2$CH(COOH)NHAc), Glyco-SNAP (1 and 2), SNOG (ON—S—CH$_2$CH(CONHCH$_2$COOH) NHCOCH$_2$CH$_2$CH(NH$_2$)COOH),K$_2$Ru(NO)Cl$_5$,SIN-10, Na$_2$[Fe(CN)$_5$NO].2H$_2$O, hydroxylamine, C$_6$H$_5$—NONOate, SPM 3672 and SPM 5185.

12. Method as claimed in claim 7 wherein said chelating agent and nitric oxide releasing moiety are linked by an organic linker group having a molecular weight of less than 1000.

13. Method as claimed in claim 7 wherein said chelating agent and nitric oxide releasing moiety are linked by an organic linker group having a molecular weight of less than 1000, said linker group comprising a linear, branched or cyclic alkylene group, or any combination thereof, or an arylene or any combination of arylene and alkylene groups, optionally interrupted by one or more heteroatoms and/or carrying bridging groups creating homo- or heterocyclic rings optionally substituted by one or more substituents selected from the group consisting of oxo, alkyl, hydroxy, alkoxy, amine, carboxyl and aryl.

14. Method as claimed in claim 7 wherein said chelating agent is DPDP, DPMP, PLED, DPDP-MOA or DPDP-DOA.

15. A dipyridoxyl based chelating agent, or a metal chelate or salt thereof, having linked thereto at least one nitric oxide releasing moiety.

16. A metal chelate as claimed in claim 15 comprising a metal ion selected from the group consisting of alkali and alkaline earth metals and metals having an atomic number of from 22–31, 42, 44 and 58–70.

17. A metal chelate as claimed in claim 16 having a $K_a$ in the range of from $10^9$ to $10^{25}$.

18. A metal chelate as claimed in claim 16 having a $K_a$ value smaller by a factor of at least $10^3$ than the $K_a$ of the corresponding iron (Fe$^{3+}$) chelate.

19. A metal chelate as claimed in claim 16 wherein said metal ion is selected from the group consisting of Na$^+$, Mn$^{2+}$, Ca$^{2+}$, Zn$^{2+}$, Cu$^{2+}$, Cu$^+$, Gd$^{3+}$ and Mg$^{2+}$.

20. A compound of formula I:

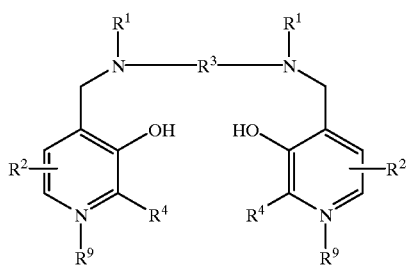

(wherein
each $R^1$ independently represents hydrogen or —$CH_2COR^5$;
$R^5$ represents hydroxy, optionally hydroxylated alkoxy, amino or alkylamido;
each $R^2$ independently represents a group —L—Z or a group —$XYR^6$, at least one group $R^2$ being a group —L—Z;
L represents a bond or an organic linker group;
Z is a nitric oxide releasing moiety;
X represents a bond, or a $C_{1-3}$ alkylene or oxoalkylene group optionally substituted by a group $R^7$;
Y represents a bond, an oxygen atom or a group $NR^6$;
$R^6$ is a hydrogen atom, a group $COOR^8$, an alkyl, alkenyl, cycloalkyl, aryl or aralkyl group optionally substituted by one or more groups selected from the group consisting of $COOR^8$, $CONR^8_2$, $NR^8_2$, $OR^8$, =$NR^8$, =O, $OP(O)(OR^8)R^7$ and $OSO_3M$;
$R^7$ is hydroxy, an optionally hydroxylated, optionally alkoxylated alkyl or aminoalkyl group;
$R^8$ is a hydrogen atom or an optionally hydroxylated, optionally alkoxylated alkyl group;
$R^9$ is absent or is a hydrogen atom, or an alkyl group optionally substituted by a carboxyl or hydroxy group;
M is a hydrogen atom or one equivalent of a physiologically tolerable cation;
$R^3$ represents a $C_{1-8}$ alkylene group, a 1,2-cycloalkylene group, or a 1,2-arylene group; and
each $R^4$ independently represents hydrogen or $C_{1-3}$ alkyl) or a metal chelate or salt thereof.

21. A compound as claimed in claim 20 wherein:
each group $R^1$ represents —$CH_2COR^5$ in which $R^5$ is hydroxy;
X is a bond or a group selected from the group consisting of $CH_2$, $(CH_2)_2$, CO, $CH_2CO$, $CH_2CH_2CO$ or $CH_2COCH_2$;
Y is a bond;
$R^6$ is a mono- or poly(hydroxy or alkoxylated) alkyl group or a group of the formula $OP(O)(OR^8)R^7$;
$R^7$ is hydroxy or an unsubstituted alkyl or aminoalkyl group;
$R^9$ is hydrogen, carboxymethyl or is absent; and
$R^3$ is ethylene.

22. A compound as claimed in claim 20 comprising N,N'-bis-(pyridoxal-5-phosphate)-ethylenediamine-N,N'-diacetic acid (DPDP), or a derivative thereof, in which either one or both phosphate groups is replaced by a nitric oxide releasing moiety.

23. A metal chelate of a compound as claimed in claim 20 comprising a metal ion selected from the group consisting of alkali and alkaline earth metals and metals having an atomic number of from 22–31, 42, 44 and 58–70.

24. A metal chelate of a compound as claimed in claim 20 having a $K_a$ in the range of from $10^9$ to $10^{25}$.

25. A metal chelate of a compound as claimed in claim 20 having a $K_a$ value smaller by a factor of at least $10^3$ than the $K_a$ of the corresponding iron ($Fe^{3+}$) chelate.

26. A metal chelate of a compound as claimed in claim 20 wherein said metal ion is selected from the group consisting of $Na^+$, $Mn^{2+}$, $Ca^{2+}$, $Zn^{2+}$, $Cu^{2+}$, $Cu^+$, $Gd^{3+}$ and $Mg^{2+}$.

27. A process for the preparation of a compound as claimed in claim 20, said process comprising at least one of the following steps:
(a) reacting a compound of formula I as defined in claim 20 in which at least one group $R^2$ is a group —$CH_2OH$ with a compound of formula II:

$$Lv-L-Z \qquad (II)$$

(where L and Z are as defined in claim 20, and Lv is a displaceable leaving group);
(b) reacting a compound of formula III

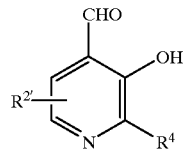

with a diamine of formula (IV)

$$H_2N-R^3-NH_2 \qquad (IV)$$

(wherein $R^3$ and $R^4$ are as defined in claim 20 and $R^{2'}$ is an optionally protected group $R^2$ as defined in claim 20);
(c) hydrogenating a compound of formula (V) obtained in step (b)

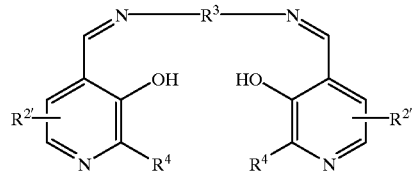

(wherein $R^3$, $R^4$ and $R^{2'}$ are as defined in claim 20);
(d) reacting a compound of formula I (wherein one or both $R^9$ groups is absent) or a compound of formula V with a reagent serving to introduce $R^9$ groups;
(e) converting a compound of formula I into a chelate complex or salt thereof;
(f) metallating or transmetallating a compound of formula I;
(g) converting a compound of formula I or a chelate thereof into a base or acid addition salt thereof or converting a salt into the free acid or base; and
(h) performing at least one of steps (a) to (f) above using reagents with protected functional groups and subsequently removing the protecting groups.

28. A pharmaceutical composition comprising a chelating agent as claimed in claim 15, or a metal chelate or salt thereof, together with at least one pharmaceutical or veterinary carrier or excipient.

29. A pharmaceutical composition comprising a compound of formula I as claimed in claim 20, or a metal chelate or salt thereof, together with at least one pharmaceutical or veterinary carrier or excipient.

30. A pharmaceutical composition comprising a dipyridoxyl chelating agent, or a derivative, metal chelate or salt thereof, together with nitric oxide or a nitric oxide releasing moiety, and at least one pharmaceutically acceptable carrier or excipient.

31. A pack containing a dipyridoxyl chelating agent, or a derivative, metal chelate or salt thereof, and separately nitric oxide or a nitric oxide releasing moiety for simultaneous, separate or sequential use in treating conditions associated with the presence of free radicals in the body, in treating microbial or retroviral infection, in treating inflammation or in reducing the cardiotoxicity of anti-tumor agents.

32. A pharmaceutical composition comprising a dipyridoxyl chelating agent carrying at least one nitric oxide releasing moiety, or a metal chelate or salt thereof, together with one or more thrombolytic agents, and at least one pharmaceutically acceptable carrier or excipient.

33. A pharmaceutical composition according to claim 32, wherein the thrombolytic agent is selected from the group consisting of aspirin, plasmin, prourokinase, streptokinase, tissue plasminogen activator, urokinase, hirudin and anti-platelet drug.

34. A pharmaceutical composition comprising a dipyridoxyl chelating agent carrying at least one nitric oxide releasing moiety, or a metal chelate or salt thereof, together with one or more anthracyclines, preferably doxorubicin, and at least one pharmaceutically acceptable carrier or excipient.

35. A pharmaceutical composition according to claim 34, wherein the anthracycline is doxorubicin.

36. Method as claimed in claim 12 wherein said chelating agent and nitric oxide releasing moiety are linked by an organic linker group having a molecular weight of less than 500.

37. Method as claimed in claim 13 wherein said chelating agent and nitric oxide releasing moiety are linked by an organic linker group having a molecular weight of less than 500.

* * * * *